(12) United States Patent
Rajaiah et al.

(10) Patent No.: US 6,475,498 B1
(45) Date of Patent: Nov. 5, 2002

(54) METHOD TO INHIBIT TARTAR AND STAIN USING DENTURE ADHESIVE COMPOSITIONS

(75) Inventors: Jayanth Rajaiah, Loveland, OH (US); Kimberly Ann Gilday-Weber, Cincinnati, OH (US); Lisa Catron Ernst, Cincinnati, OH (US); Larry Gregory Martin, Cincinnati, OH (US); Marjorie Samuel Becus, Loveland, OH (US); Timothy Sadley Owens, Loveland, OH (US); Ann Maria Case, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/716,820

(22) Filed: Nov. 20, 2000

Related U.S. Application Data

(60) Provisional application No. 60/169,558, filed on Dec. 8, 1999.

(51) Int. Cl.[7] .................. A61K 6/08; C08L 33/08; C09J 7/00; C08F 222/06; A61C 13/23
(52) U.S. Cl. .................. 424/401; 424/49; 433/180; 523/120; 106/35
(58) Field of Search .................. 424/49–58, 401; 106/35; 523/120; 433/180

(56) References Cited

U.S. PATENT DOCUMENTS

| | | | |
|---|---|---|---|
| 3,429,963 A * | 2/1969 | Shedlovsky | 424/56 |
| 3,736,274 A | 5/1973 | Schoenholz et al. | |
| 3,941,772 A | 3/1976 | Ploger et al. | 260/239 |
| 3,956,480 A * | 5/1976 | Dichter et al. | 424/54 |
| 3,960,888 A | 6/1976 | Ploger et al. | 260/326.5 |
| 3,988,443 A | 10/1976 | Ploger et al. | 424/200 |
| 4,138,477 A | 2/1979 | Gaffar | 424/52 |
| 4,315,779 A | 2/1982 | Heyd et al. | 106/35 |
| 4,627,977 A | 12/1986 | Gaffar et al. | 424/52 |
| 5,037,924 A * | 8/1991 | Tazi et al. | 526/272 |
| 5,055,046 A | 10/1991 | Chaundhuri et al. | |
| 5,096,699 A | 3/1992 | Gaffar et al. | 424/49 |
| 5,192,362 A | 3/1993 | Harvey et al. | 106/35 |
| 5,208,009 A | 5/1993 | Gaffar et al. | 424/49 |
| 5,304,616 A | 4/1994 | Rajaiah et al. | |
| 5,334,375 A * | 8/1994 | Nabl et al. | 424/52 |
| 5,368,844 A | 11/1994 | Gaffar et al. | 424/49 |
| 5,424,058 A | 6/1995 | Rajaiah et al. | |
| 5,543,443 A | 8/1996 | Rajaiah et al. | |
| 5,658,586 A | 8/1997 | Rajaiah et al. | |
| 5,750,591 A | 5/1998 | Clarke et al. | 523/120 |
| 5,753,723 A | 5/1998 | Chang et al. | 523/120 |
| 5,872,160 A | 2/1999 | Rajaiah et al. | |
| 5,872,161 A | 2/1999 | Rajaiah et al. | |
| 5,877,233 A | 3/1999 | Rajaiah et al. | |
| 5,880,172 A | 3/1999 | Rajaiah et al. | |
| 6,046,291 A * | 4/2000 | Zhang et al. | 526/272 |
| 6,069,188 A | 5/2000 | Rajaiah et al. | |
| 6,117,416 A * | 9/2000 | Prosise et al. | 424/49 |
| 6,124,374 A * | 9/2000 | Kolias et al. | 523/160 |
| 6,315,987 B1 * | 11/2001 | Plochocka | 424/49 |
| 6,355,706 B1 | 3/2002 | Rajaiah et al. | |

FOREIGN PATENT DOCUMENTS

| | | | |
|---|---|---|---|
| DE | 2229446 | 12/1972 | A61K/7/16 |
| WO | WO 99/18140 | 4/1999 | C08F/222/04 |
| WO | WO 99/42079 | 8/1999 | A61K/6/00 |
| WO | WO 00/00165 | 1/2000 | A61K/7/16 |
| WO | WO 00/33792 | 6/2000 | |

OTHER PUBLICATIONS

Wilson, M, et al; Prevention of Bacterial Adhesion to Denture Acrylic, 1989, Journal of Dentistry—17: No. 4 p. 166–170.

* cited by examiner

Primary Examiner—Shep K. Rose
(74) Attorney, Agent, or Firm—Betty J. Zea

(57) ABSTRACT

The present invention relates to a method of reducing, controlling, inhibiting, preventing, protecting against, or minimizing calculus, tartar, plaque, or stain, in the oral cavity, by applying a denture adhesive composition to the oral cavity, the denture adhesive composition comprising:

(a) a safe and effective adhesive amount of a denture adhesive component; and (b) a safe and effective amount of a non-aqueous denture adhesive carrier.

16 Claims, No Drawings

US 6,475,498 B1

METHOD TO INHIBIT TARTAR AND STAIN USING DENTURE ADHESIVE COMPOSITIONS

This application claims the benefit of U.S. Provisional Application No. 60/169,558, filed Dec. 8, 1999.

BACKGROUND OF THE INVENTION

Ordinary removable dentures, dental plates and the like, comprise teeth mounted in a suitable plate or base. Denture stabilizers are used to fill the interstices between the dentures and the gums or tissues. Prior to placement of the denture in the oral cavity, a denture stabilizer is applied to the denture-plate surface which, for a perfect fit, should uniformly contact the gums and mucous tissues. The denture stabilizer is formulated not only for its adherent properties, but also to provide a cushion or gasket between the denture and the gums or tissues, thereby positioning the denture securely in the oral cavity.

Considerable effort has been made over the years to develop improved denture adhesive compositions. Both synthetic and natural polymers and gums have been used alone, in combination, and in combination with various adhesives and other materials in an attempt to improve hold and reduce oozing of the adhesive from under the dental plate, messiness and difficulty of removing the residual adhesive from the mouth and dentures. For example, alkyl vinyl ether-maleic copolymers and salts thereof are known for providing good hold in denture adhesive compositions. Such disclosures include: U.S. Pat. No. 3,003,988, Germann et al., issued Oct. 10, 1961; U.S. Pat. No. 4,980,391, Kumar et al., issued Dec. 25, 1990; U.S. Pat. No. 5,073,604, Holeva et al., issued Dec. 17, 1991; U.S. Pat. No. 5,525,652, Clarke, issued Jun. 11, 1996; U.S. Pat. No. 5,340,918, Kittrell et al., issued Aug. 23, 1994; U.S. Pat. No. 5,830,933, Synodis et al., issued Nov. 3, 1998.

In addition to adhesion, it is desirable to deliver anticalculus or antitartar benefits in a denture adhesive composition especially for those denture wearers who still have some natural teeth remaining. Tartar is a deposit which forms on the surfaces of teeth. Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris, and microorganisms.

It is generally known that certain polysaccharides applied via an aqueous carrier may prevent specific types of bacteria from adhering to denture acrylic. Wilson et al., Prevention of bacterial adhesion to denture acrylic, *J. Dent.* 1989; Vol. 17; p. 166–70 and U.S. Pat. No. 5,192,362, Harvey et al., issued Mar. 9, 1993. However, only aqueous compositions of polysaccharides were tested and applied to acrylic strips. In addition, the '362 patent is not concerned with anhydrous compositions or the securing of dentures. The dentures are coated from an aqueous suspension. In addition U.S. Pat. No. 4,315,779, issued Feb. 16, 1982, Heyd et al., teaches a non-adhesive denture composition for improving the fit and adaptation of dentures to the oral cavity comprising cellulose polymer or alginate, a demulcent selected from glycerine, sorbitol, and propylene glycol, and 50% to 95% by weight water. This reference also teaches that these compositions prevent the build-up of undesirable deposits such as plaque and have antibacterial and/or mycostatic effects. Despite these teachings, a method of reducing or preventing calculus, plaque, and/or stain, in the oral cavity, by applying a non-aqueous denture adhesive composition to the oral cavity, has not been suggested.

Despite the above-noted technologies as well as others, a need still exists for denture stabilizing compositions providing both improved hold and anticalculus or antitartar benefits to the denture wearer. The present invention relates to a method of reducing, controlling, inhibiting, preventing, protecting against or minimizing calculus, tartar, plaque, and/or stain, in the oral cavity, by applying a non-aqueous denture adhesive composition comprising a denture adhesive component and a non-aqueous vehicle. These compositions provide the above benefits, while providing superior denture hold, holding dentures in place for a prolonged period of time.

SUMMARY OF THE INVENTION

The present invention relates to a method of reducing, controlling, inhibiting, preventing, protecting against or minimizing calculus, tartar, plaque, and/or stain, in the oral cavity, by applying a denture adhesive composition comprising:

(a) a safe and effective adhesive amount of a denture adhesive component; and (b) a safe and effective amount of a non-aqueous denture adhesive carrier.

DETAILED DESCRIPTION OF THE INVENTION

A detailed description of essential and optional components of the present invention is given below.

Definitions

The term "safe and effective adhesive amounts" as used herein means an amount sufficient to provide adherence to the oral cavity and/or provide adherence of a dental prosthesis to the oral cavity, without toxicity to the user or damage to oral tissue.

By "safe and effective amount", as used herein, is meant an amount of an agent high enough to significantly (positively) modify the condition to be treated, but low enough to avoid serious side effects (at a reasonable benefit/risk ratio), within the scope of sound medical/dental judgment. The safe and effective amount of an agent may vary with the particular condition being treated, the age and physical condition of the patient being treated, the severity of the condition, the duration of treatment, the nature of concurrent therapy, the specific form of the source employed, and the particular vehicle from which the agent is applied.

The term "AVE/MA" as used herein refers to alkyl vinyl ether-maleic acid or anhydride copolymer. The term "AVE/MA/IB" refers to terpolymers with alkyl vinyl ether, maleic acid or anhydride, and isobutylene. The term "mixed polymer salts" or "mixed salts", as used herein, refers to salts of AVE/MA and/or salts of AVE/MA/IB where at least 2 different cations are mixed on the same polymer with each other or with other salts.

The term "free acid" or "FA" component, as used herein, refers either to the unreacted carboxyl groups (—COOH) of AVE/MA copolymer and/or AVE/MA/IB plus any other monovalent cations of carboxyl groups (e.g., COONa) of the polymer. Monovalent cations include Group IA cations, such as sodium, potassium, hydrogen, etc. Preferably, the term "free acid" refers to the unreacted carboxyl groups (—COOH) of AVE/MA and/or AVE/MA/IB plus sodium and potassium cations. More preferably, the term "free acid" refers only to the unreacted carboxyl groups (—COOH) of the AVE/MA and/or AVE/MA/IB.

The percentages used herein to describe the cationic salt function of the alkyl vinyl ether-maleic acid or anhydride copolymers are defined as the stoichiometric percent of the total initial carboxyl groups reacted on the polymer.

All other percentages used herein are by weight of the composition unless otherwise indicated.

Denture Adhesive Components

The present invention comprises a safe and effective adhesive amount of a denture adhesive component, generally at a level of from about 10% to about 90%, in another embodiment from about 15% to about 70%, and in another embodiment from about 20% to about 50%, by weight of the composition. In one embodiment the compositions of the present invention comprise at least 20 percent by weight, and in another embodiment at least 30 percent by weight of the composition, of a denture adhesive component.

"Denture adhesive components" can be any bioadhesive materials and include natural gums, synthetic polymeric gums, AVE/MA, salts of AVE/MA, AVE/MA/IB, salts of AVE/MA/IB, copolymer of maleic acid or anhydride and ethylene and salts thereof, copolymer of maleic acid or anhydride and styrene and salts thereof, copolymer of maleic acid or anhydride and isobutylene and salts thereof, polyacrylic acid and polyacrylates thereof, polyitaconic acid and salts thereof, synthetic polymers, mucoadhesive polymers, water-soluble hydrophilic colloids or polymers having the property of swelling upon exposure to moisture to form a mucilaginous mass, hydrophilic polymers, saccharide derivatives, cellulose derivatives, any adhesive material employed in denture stabilizing compositions, and mixtures thereof. Examples of such materials include karaya gum, guar gum, gelatin, algin, sodium alginate, tragacanth, chitosan, polyethylene glycol, polyethylene oxide, acrylamide polymers, carbopol, polyvinyl alcohol, polyamines, polyquarternary compounds, ethylene oxide polymers, polyvinylpyrrolidone, cationic polyacrylamide polymers, AVE/MA, AVE/MA/IB, mixed salts of AVE/MA, mixed salts of AVE/MA/IB, and mixtures thereof.

In one embodiment the adhesives are salts of AVE/MA, salts of AVE/MA/IB, mixed salts of AVE/MA, mixed salts of AVE/MA/IB, cellulose derivatives (such as methylcellulose, carboxymethylcellulose, hydroxyethylcellulose, hydroxypropylcellulose, hydroxy-propylmethylcellulose, and mixtures thereof), polyethylene glycol, polyethylene oxide, karaya gum, sodium alginate, chitosan, polyvinyl alcohol, and mixtures thereof. In yet another embodiment, the adhesive component is mixed salts of AVE/MA, cellulose derivatives and mixtures thereof.

Alkyl Vinyl Ether-Maleic Copolymer

In one embodiment of the invention the denture adhesive is AVE/MA or salts of AVE/MA. The alkyl vinyl ether-maleic acid co-polymer comprises or consists essentially of the repeated structural unit:

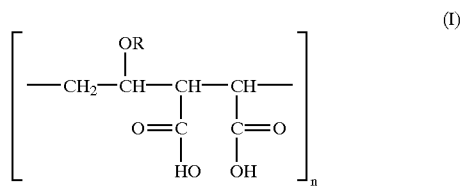

wherein R represents an alkyl radical, preferably a $C_1$ to $C_5$ alkyl radical, n is an integer greater than one representing the number of repeated occurrences of the structural unit in a molecule of the polymer.

In one embodiment, the adhesive component is AVE/MA and salts thereof, preferably mixed salts of AVE/MA, wherein the copolymer contains a cationic salt function comprising a cation selected from the group consisting of Group IA and Group 2A cations of the periodic table, yttrium, titanium, zirconium, vanadium, chromium, manganese, iron, nickel, copper, zinc, boron, aluminum, cations and mixtures thereof. In another embodiment, the adhesive component is a mixed salt of AVE/MA containing a cationic salt function comprising a cation selected from the group consisting of strontium, zinc, iron, boron, aluminum, vanadium, chromium, manganese, nickel, copper, yttrium, titanium, magnesium, calcium, sodium, cations and mixtures thereof, and in yet another embodiment the the cation is selected from the group consisting of strontium, zinc, iron, magnesium, calcium, sodium, cations, and mixtures thereof.

AVE/MA contains, in one embodiment, a cationic salt function comprising from about 5% to about 50%, in another embodiment, from about 10% to about 40%, in yet another embodiment, from about 10% to about 35% (of the total initial carboxyl groups reacted) zinc cations. These zinc cations can be mixed with other cations selected from the group consisting of: from about 5% to about 65%, preferably from about 10% to about 60%, strontium cations, from about 0.001% to about 2.5%, preferably from about 0.01% to about 2% of iron, boron, aluminum, vanadium, chromium, manganese, nickel, copper, yttrium, and/or titanium cations, from about 5% to about 65%, preferably from about 15% to about 50% of calcium and/or magnesium cations.

AVE/MA and salts thereof and AVE/MA/IB and salts thereof, are also described in U.S. Pat. No. 5,073,604 to Holeva et al., issued Dec. 17, 1991; U.S. Pat. No. 5,525,652, issued Jun. 11, 1996, Clarke et al.; U.S. Pat. No. 4,758,630, issued Jul. 19, 1988, Shah et al.; U.S. Pat. No 5,304,616, issued Apr. 19, 1994, Rajaiah et al.; U.S. Pat. No. 5,424,058, issued Jun. 13, 1995, Rajaiah; U.S. Pat. No. 5,424,058, issued Jun. 13, 1995, Rajaiah et al.; U.S. Pat. No. 4,758,630, issued Jul. 19, 1988, Shah et al.; U.S. Pat. No. 5,830,933, issued Nov. 3, 1998, Synodis et al.; U.S. Pat. No. 2,047,398, issued Jul. 14, 1936, Voss et al.; U.S. Pat. No. 3,003,988, issued Oct. 10, 1961, Germann et al.; U.S. Pat. No. 5,880,172, Rajaiah et al., issued Mar. 9, 1999; U.S. Pat. No. 5,900,470, Prosise et al., issued May 4, 1991; U.S. Pat. No. 5,037,924, Tazi et al., issued Jan. 21, 1992; U.S. Pat. No. 5,082,913, Tazi et al, issued Jan. 21, 1992; all of which are incorporated herein by reference in their entirety. Salts of AVE/MA are also described in P&G copending applications Ser. Nos: 06/152,158, filed Sep. 2, 1999, Rajaiah et al.; Ser. No. 60/129,164, filed Apr. 14, 1999, Rajaiah et al.; Ser. No. 60/129,162, filed Apr. 14, 1999, Rajaiah et al.; Ser. No. 60/152,122, filed Sep. 2, 1999, Rajaiah et al.; Ser. No. 09/291,554, filed Apr. 14, 1999, Rajaiah et al.; Ser. No. 09/389,209, filed Sep. 2, 1999, Rajaiah et al.; and Ser. No. 09/389,210, filed Sep. 2, 1999, Rajaiah et al., all of which are incorporated herein by reference in their entirety.

In one embodiment the free acid level of the salts of the AVE/MA or AVE/MA/IB is at least about 36%, in another embodiment is from about 36% to about 60%, and even in another embodiment is from about 40% to about 55%, of the total initial carboxyl groups of the copolymer or terpolymer.

The specific viscosity of the starting copolymer acid or copolymer anhydride is from about 1.2 to about 14, when preferably measured in a 1% weight/volume solution in MEK (methyl ethyl ketone) at 25° C. Other methods and solvents can be used to measure the specific viscosity such as a 1% weight/volume solution in DMF (dimethyl formamide) at 25° C. and a 1% weight/volume solution in 2-butanone at 25° C.

Suitable AVE/MA copolymers may be prepared by well-known methods of the prior art; see, for example, U.S. Pat. No. 2,782,182, and U.S. Pat. No. 2,047,398, both of which are incorporated by reference herein in their entirety.

The salt form of the subject polymers may be prepared by the interaction of the acid or anhydride polymer with at least one cationic salt function as described above, having a functional group typical of reactants of a carboxylic acid, such as, for example, the hydroxide, oxide, acetate, halide, lactate, etc. in an aqueous medium. In one embodiment, the zinc oxide, strontium carbonate, iron sulfate n-hydrate, etc. are utilized.

Ions that form toxic, irritating or contaminating by-products should be avoided, or special precautions and treatment provided to assure the removal and absence of such by-products from the polymeric salt end-product. The particular compound used should be substantially pure to assure obtaining a substantially pure, polymeric salt end-product.

The salt form of the polymer can be made by mixing the salts (sodium hydroxide, zinc oxide, strontium carbonate, ferric sulfate n-hydrate, calcium hydroxide and/or magnesium oxide, etc.) in an aqueous dispersion. This is combined with the powder alkyl vinyl ether-maleic acid or anhydride copolymer, in the form of a slurry, in an amount sufficient to provide the desired cationic content desired in the end-product. This is done at ambient temperature and then slowly heated to 70°–95° C. with continuous vigorous mixing so as to prevent localized precipitation of the cationic polymeric salt; mixing is continued to ensure that all the salt forming compound is reacted with the copolymer.

Alternatively, the AVE/MA copolymer is hydrolyzed and neutralized in an aqueous mixture or slurry of one or more divalent and/or monovalent metal bases by heating the copolymer/base mixture to a temperature ranging from about 45° C. to about 100° C.

In either of the above processes, the resulting slurry or solution is transferred to shallow stainless steel drying trays and placed in a forced air mechanical convection oven at 60–70° C. for a time sufficient to evaporate the reaction medium (water) and remove water from the copolymer (about 18–24 hours). Alternatively, the resulting slurry or solution can be drum-dried at 100° to 200° C. with hot steam to evaporate the water content and recover the copolymer in the flake form. After drying, the polymer forms brittle flakes which can easily be peeled off from the trays or drum surface and ground to a fine powder as desired to provide satisfactory denture stabilizing properties. Methods of making these mixed salts of AVE/MA polymers are further disclosed in U.S. Pat. No. 5,073,604, Holeva et al., issued Dec. 17, 1991 and U.S. Pat. No. 5,872,161, Liang et al., issued Feb. 16, 1999, both of which are herein incorporated by reference in their entirety.

Non-Aqueous Denture Adhesive Carrier

The non-aqueous denture adhesive carrier is selected from the group consisting of a non-aqueous vehicle and a non-adhesive self supporting layer. The level of non-aqueous vehicle is from 10% to about 90%, in another embodiment is from about 20% to about 80%, and in yet another embodiment is from about 20% to about 60%, by weight of the composition.

Non-aqueous Vehicles

The non-aqueous vehicle is generally any chemical in any physical form that does not contain water. The non-aqueous vehicle is selected from the group consisting of liquid petrolatum, petrolatum, mineral oil, glycerin, natural and synthetic oils, fats, silicone and silicone derivatives, polyvinylacetate, natural and synthetic waxes such as animal waxes like beeswax, lanolin and shellac, hydrocarbons, hydrocarbon derivatives, vegetable oil waxes such as carnauba, candelilla and bayberry wax, vegetable oils such as caprylic/capric triglycerides, in another embodiment is selected from the group consisting of liquid petrolatum, petrolatum, mineral oil, vegetable oils such as corn, soy bean, cottonseed, castor, palm and coconut oils and animal oil such as fish oil and oleic acid, and mixtures thereof; and in yet another embodiment is mineral oil.

Caprylic/capric triglycerides are triglycerides of medium chain fatty acids where the —C═O—R group is 8–10 carbons and is obtained by the addition of glycerol to a mixture of capric and caprylic acids:

Caprylic acid: $CH_3(CH_2)_6CO_2H$

Capric acid: $CH_3(CH_2)_8CO_2H$

Therefore, vegetable oils comprised of saturated medium chain fatty acids such as caprylic acid, capric acid and mixtures thereof, can be used in the present invention. These vegetable oils and other non-aqueous vehicles for denture adhesive compositions are further described in U.S. Pat. No. 5,561,177, issued on Oct. 1, 1996, Khaledi et al., which is incorporated herein by reference in its entirety.

Non-Adhesive Self-Supporting Layer

The non-aqueous carrier can comprise at least one non-adhesive self-supporting layer. The non-adhesive self-supporting layer is characterized by its ability to maintain strength and provide integrity for the adhesive composition in the presence of water and/or saliva. The non-adhesive self-supporting layer may include materials such as polyester, polypropylene, nylon, rayon, cellulose acetate, non-adhesive cellulose derivatives, cloth, fibrous fleece, paper, plastic, leather, microcrystalline wax, synthetic fibers, natural fibers, and mixtures thereof. Preferred are non-adhesive cellulose derivatives, polyester, polypropylene, nylon, rayon, cloth, paper, microcrystalline wax, and mixtures thereof. More preferred are polyester, polypropylene, rayon, nylon, cloth and paper.

The non-adhesive self-supporting layer may be in any physical form suitable for providing strength and/or integrity to the present adhesive compositions. Such physical forms include non-woven, woven, continuous, chopped, foam, and combinations thereof. In addition, the non-adhesive self-supporting layer may be formed by any process commonly known in the art. Such processes include un-bonded, spraybonded, spun-bonded, needle-punched, carded, thermal bonded hydroentangled, meltblown, aperture print bonded, needled, wet-laid, dry-laid, and combinations thereof.

The present denture adhesive compositions which comprise a non-adhesive self-supporting layer may also comprise a coating which is sticky to dry dentures and, if present, will be placed on one side of the denture adhesive composition. Compositions suitable for use as this type of adhesive layer include silicones, rubbers, petrolatum, natural polymers, synthetic polymers, and mixtures thereof. The adhesive layer may be present at a level of from about 0% to about 70%, and in another embodiment from about 0.5% to about 20%, by weight of the composition.

Miscellaneous Carriers

Other suitable ingredients include colorants, preservatives (such as methyl and propyl parabens), thickeners such as silicon dioxide, and polyethylene glycol. Colorants, preservatives, thickeners may be present at levels of from about 0% to about 20%, by weight of the composition. Examples of colorants include the paste-like Opatint® products from Colorcon (West Point, Pa.) which contain lakes and/or dyes dispersed in liquids such as mineral oil and/or petrolatum. These lakes and dyes are selected from the group consisting of D&C Red 27, D&C Red 22, D&C Red 28, FD&C Red 3 and FD&C 40, Opatint-OD 1646, Opatint OD-1774, CAS#13473-26-2, 18472-87-2, 16423-68-0, 548-26-5, 2379-74-0, 915-67-3, 25956-17-6, and fluorescein dyes with chlorine and/or bromine. Specifically, colorants include fluorescein dyes with chlorine and/or bromine such as tetrabromo-tetrachloro-fluorescein, disodium salt of tetrabromo-tetrachloro-fluorescein. In another embodiment the colorants are selected from the group consisting of fluorescein dyes with chlorine and/or bromine, such as tetrabromo-tetrachloro-fluorescein, disodium salt of tetrabromo-tetrachloro-fluorescein. Opatint OD-1646, D&C Red 27, D&C Red 28, and mixtures thereof. In another embodiment the colorants are selected from the group consisting of Opatint OD-1646, D&C Red 27, D&C Red 28, and mixtures thereof. In even another embodiment the colorant is Opatint OD-1646, CAS#13473-26-2 is 2', 4', 5', 7'-tetrabromo-4,5,6, 7-tetrachlorofluorescin, 18472-87-2 is disodium salt of 2', 4', 5', 7'-tetrabromo-4,5,6, 7-tetrafluorescein, 16423-68-0 is 3'6'-Dihydroxy-2', 4', 5', 7-tetraiodosprio[isobenzofuran- 1(3H),9'-(9-H)]xanthen]-3'-one-disodium salt, 548-26-5 is tetrabromo-3',6'-dihydroxy-, disodium salt, 2379-74-0 also known as Japan Red 226 and Pigment Red 181 and as 5,5'-Dichloro-3,3'-dimethyl-Thioindigo, 915-67-3 is 6-hydroxy-5-[(2-methoxy-5-methyl-4-sulfophenyl)azo]-2-naphthalene-sulfonic acid disodium salt, 25956-17-6 is 6-Hydroxy-5-[(2-Methoxy-5-Methyl-4-Sulfophenyl)Azo]-2-Naphthalenesulfonic Acid, disodium salt. The level of colorant is in another embodiment from 0 to about 5%, in even another embodiment from about 0.02% to about 2%, and in even another embodiment is from about 0.05% to about 1% by weight of the composition.

Plasticizers

In addition one or more toxicologically-acceptable plasticizers may also be included in the present compositions. The term "toxicologically-acceptable", as used herein, is used to describe materials that are suitable in their toxicity profile for administration to humans and/or lower animals. Plasticizers that may be used in the present compositions include dimethyl phthalate, diethyl phthalate, dioctyl phthalate, glycerin, diethylene glycol, triethylene glycol, Igepal®, Gafac®, sorbitol, tricresyl phosphate, dimethyl sebacate, ethyl glycolate, ethylphthalyl ethyl glycolate, o- and p-toluene ethyl sulfonamide, and mixtures thereof. Plasticizers may be present at a level of from about 0% to about 70%, in another embodiment from about 1% to about 30%, by weight of the compositions.

Flavors, Fragrance, Sensates

The compositions of the present invention may also include one or more components which provide flavor, fragrance, and/or sensate benefit (warming or cooling agents). Suitable components include natural or artificial sweetening agents, menthol, menthyl lactate, wintergreen oil, peppermint oil, spearmint oil, leaf alcohol, clove bud oil, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof, as well as coolants. The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979; the disclosure of both are herein incorporated by reference in their entirety. These agents may be present at a level of from about 0% to about 50%, by weight of the composition.

Other Optional Ingredients

The denture adhesive compositions may also be used as a denture adhesive and/or bioadhesive and comprise one or more therapeutic actives suitable for topical administration. Therapeutic actives may be present at a level of from about 0% to about 70%, by weight of the composition, and in one embodiment from about 1% to about 20% by weight of the composition. Therapeutic actives include antimicrobial agents such as iodine, tricolsan, peroxides, sulfonamides, bisbiguanides, or phenolics; antibiotics such as tetracycline, neomycin, kanamycin, metronidazole, cetylpyridium chloride, or clindamycin; anti-inflammatory agents such as aspirin, acetaminophen, naproxen and its salts, ibuprofen, ketorolac, flurbiprofen, indomethacin, eugenol, or hydrocortisone; dentinal desensitizing agents such as potassium nitrate, strontium chloride or sodium fluoride; fluorides such as sodium fluoride, stannour fluoride, MFP; anesthetic agents such as lidocaine or benzocaine; anti-fungals such as those for the treatment of candida albicans; aromatics such as camphor, eucalyptus oil, and aldehyde derivatives such as benzaldehyde; insulin; steroids; herbal and other plant derived remedies; baking soda, and anti-neoplastics. It is recognized that in certain forms of therapy, combinations of these agents in the same delivery system may be useful in order to obtain an optimal effect. Thus, for example, an antimicrobial and an anti-inflammatory agent may be combined in a single delivery system to provide combined effectiveness.

Process for Preparation of the Composition

A process for preparing denture adhesive compositions of the present invention (creams, powders, wafers, non-aqueous liquids, aerosols, pastes) comprises conventional methods disclosed in the art. Conventional methods are taught in U.S. Pat. No. 5,525,652, issued Jun. 11, 1996, Clarke et al.; U.S. Pat. No. 3,003,988, issued Oct. 10, 1961, Germann et al.; U.S. Pat. No. 5,073,604, Holeva et al., issued Dec. 17, 1991; and U.S. Pat. No. 5,872,161, Liang et al., issued Feb. 16, 1999, all of which are herein incorporated by reference in their entirety.

A process for the preparation of the present denture adhesive compositions comprising a non-adhesive self-supporting layer, comprises coating a weighed amount of the adhesive components onto the non-adhesive self-supporting layer. This process is disclosed in U.S. Pat. No. 5,877,233, Liang et al, issued Mar. 2, 1999; U.S. Pat. No. 5,872,160, issued Feb. 16, 1999, Liang et al.; U.S. Pat. No. 5,880,172, Rajaiah et al., filed Oct. 25, 1996, all of which are incorporated herein by reference in their entirety.

Composition Use

The adhesive compositions may be in the form of a powder, cream, paste, non-aqueous liquid, aerosol, and/or wafer. Powder forms are sprinkled on a dental prosthesis, moistened and then inserted into the oral cavity. Wafer compositions (denture adhesive compositions with a self supporting layer) are thoroughly moistened and applied to denture prosthesis which are then inserted into the oral cavity. Cream and paste compositions are generally applied to the denture prosthesis and thereafter the denture is secured to the oral cavity.

The following examples further describe and demonstrate embodiments within the scope of the present invention. The examples are given solely for the purpose of illustration and are not to be construed as limitations of the present invention. Many variations of these are possible without departing from the spirit and scope of the invention.

EXAMPLE I

A denture wearer places from 0.1 to 5 grams of any of the cream composition described below on their denture. Then the subject inserts the denture into his/her mouth and presses it into place. After applying this composition, the composition prevents, minimizes, protects-against and/or inhibits the buildup of calculus, tartar, plaque, and/or stain, in the oral cavity.

|  | A Grams | B Grams | C Grams | D Grams | E Grams |
|---|---|---|---|---|---|
| White Mineral Oil | 23.93 | | | | |
| Petrolatum, White | 21.87 | | | | |
| Carboxymethylcellulose Sodium | 20.00 | 20.00 | 20.00 | 20.00 | 20.00 |
| Silicon Dioxide, Colloidal | 1.14 | 1.14 | 1.14 | 1.14 | 1.14 |
| Colorant (Opatint OD-1646) | 0.06 | 0.06 | 0.06 | 0.06 | 0.06 |
| Any salt, acid or anhydride of AVE/MA and/or AVE/MA/IB | 33.00 | 33.00 | 33.00 | 33.00 | 33.00 |
| Polydimethyl siloxane[1] | | 45.8 | | | |
| Corn Oil | | | 45.8 | | |
| Fish Oil | | | | 45.8 | |
| Vegetable Oil | | | | | 45.8 |

[1]Dow Corning Fluids.

The colorant red dye and non-aqueous carrier are weighed, heated and mixed in a glass jar at 50 to 60° C. until visually uniform. Then the powders are weighed and shake-blended (colloidal silicon dioxide, CMC, AVE/MA, AVE/MA/IB) together in a container. Thereafter, the powders are mixed into the liquid with a spatula until visually a uniform pink cream. The above compositions may be modified by increasing or decreasing the level of AVE/MA or AVE/MA/IB by 0 to 15 grams, petrolatum by 0 to 15 grams, colorant by 0 to 5 grams and/or the CMC by 0 to 15 grams. The above compositions can also be modified by using any other non-aqueous vehicle of the present invention. The colorant, Opatint OD 1646, can be substituted with Opatint OD 1774, Red D&C 27, Red D&C 28 or any other colorant listed above in the specification.

EXAMPLES II

A denture wearer places from 0.1 to 5 grams of any of the cream composition described below on their denture. Then the subject inserts the denture into his/her mouth and presses it into place. After applying this composition, the composition prevents, minimizes, protects-against,or inhibits the buildup of calculus, tartar, plaque, and/or stain, in the oral cavity. Denture adhesive cream compositions include the following:

|  | A Grams | B Grams | C Grams | D Grams | E Grams | F Grams |
|---|---|---|---|---|---|---|
| White Mineral Oil | 23.93 | 23.93 | 23.93 | 23.93 | 23.93 | 23.93 |
| Petrolatum, White | 21.87 | 21.83 | 21.73 | 21.43 | 20.93 | 21.43 |
| Carboxymethylcellulose Sodium | 20.00 | 20.00 | 20.00 | 20.00 | 20.00 | 20.00 |
| Silicon Dioxide, Colloidal | 1.14 | 1.14 | 1.14 | 1.14 | 1.14 | 1.14 |
| Colorant (Opatint OD 1646) | 0 | 0.06 | 0.5 | 0.5 | 5.0 | 0.06 |
| Spray-dried slo-release Peppermint | | | | | | 0.15 |
| Menthol | | | | | | 0.12 |
| Menthyl Lactate | | | | | | 0.17 |
| Ca/Zn salt of AVE/MA | 33.00 | 33.00 | 33.00 | 33.00 | 33.00 | 33.00 |

The red dye and non-aqueous carrier are weighed, heated and mixed in a glass jar at 50 to 60° C. until visually uniform. Then the powders are weighed and shake-blended (colloidal silicon dioxide, CMC, AVE/MA,) together in a container. Thereafter, the powders are mixed into the liquid with a spatula until visually a uniform cream. The above compositions can be modified by increasing or decreasing the level of AVE/MA by 0 to 15 grams, petrolatum by 0 to 15 grams, colorant by 0–5 grams, flavors and sensates by 0 to 2 grams, and/or the CMC by 0 to 15 grams. The above compositions can also be modified by using any other non-aqueous carrier of the present invention. The colorant, Opatint OD 1646, may be substitued with Opatint OD 1774, Red D&C 27, Red D&C 28, or any other colorant listed above in the specification.

What is claimed is:

1. A method of reducing, controlling, inhibiting preventing, protecting against, or minimizing calculus, tartar, plaque, or stain, in the oral cavity, by applying a denture adhesive composition to the oral cavity of a denture wearer in need thereof, the denture adhesive composition comprising:
   (a) at least 20% by weight of the composition of a polymer wherein the polymer is a denture adhesive component selected from the group consisting of natural gums, synthetic polymeric gums, karaya gum, guar gum, gelatin, algin, sodium alginate, tragacanth, chitosan, polyethylene glycol, acrylamide polymers, polyvinyl alcohol, polyamines, polyquarternary compounds, ethylene oxide polymers, polyvinylpyrrolidone, cationic polyacrylamide polymers, saccharide derivatives, cellulose derivatives, salts of AVE/MA, AVE/MA, and mixtures thereof; and (b) a safe and effective amount of a non-aqueous denture adhesive carrier;

wherein the composition is essentially free of anticalculus agent, antitartar agent, antiplaque agent or antistain agent.

2. The method of claim 1 wherein the denture adhesive component is selected from the group consisting of karaya gum, guar gum, gelatin, algin, sodium alginate, tragacanth, chitosan, AVE/MA, salts of AVE/MA, cellulose derivatives, and mixtures thereof.

3. The method of claim 2 wherein the denture adhesive component is a salt of AVE/MA, and mixtures thereof, the salt containing a cationic salt function comprising a cation selected from the group consisting of Group IA and Group 2A cations of the periodic table, yttrium, titanium, zirconium, vanadium, chromium, manganese, iron, nickel, copper, zinc, boron, aluminum, sodium, and mixtures thereof.

4. The method of claim 3 wherein the cation is selected from the group consisting of strontium, zinc, iron, magnesium, calcium, sodium, and mixtures thereof.

5. The method of claim 4 wherein the level of denture adhesive component is from 20% to about 50%, by weight of the composition.

6. The method of claim 4 wherein the denture adhesive component is a cellulose derivative selected from the group consisting of hydroxyethylcellulose, hydroxypropylcellulose, hydroxypropylmethyl-cellulose, sodium carboxymethylcellulose, and mixtures thereof.

7. The method of claim 6 wherein the cellulose derivative is carboxymethylcellulose.

8. The method of claim 1 wherein the non-aqueous denture adhesive carrier is selected from the group consisting of a non-aqueous vehicle and a non-adhesive self supporting layer.

9. The method of claim 8 wherein the carrier is a non-aqueous vehicle is selected from the group consisting of liquid petrolatum, petrolatum, mineral oil, natural and synthetic oils, fats, natural and synthetic waxes, beeswax, lanolin, shellac, hydrocarbons, hydrocarbon derivatives, vegetable oil waxes, carnauba, candelilla, bayberry wax, caprylic/capric triglycerides, and mixtures thereof.

10. The method of claim 9 wherein the non-aqueous vehicle is selected from the group consisting of liquid petrolatum, petrolatum, mineral oil, corn oil, soybean oil, cottonseed oil, and mixtures thereof at a level of from about 20% to about 80%, by weight of the composition.

11. The method of claim 10 wherein the non-aqueous vehicle is mineral oil, petrolatum, and mixtures thereof.

12. The method of claim 8 wherein the carrier is a non-adhesive self-supporting layer.

13. The method of claim 12 wherein the non-adhesive self-supporting layer is selected from the group consisting of polyester, polypropylene, nylon, rayon, cellulose acetate, non-adhesive cellulose derivatives, cloth, fibrous fleece, paper, plastic, leather, synthetic fibers, natural fibers, and mixtures thereof.

14. The method of claim 1 additionally comprising a colorant selected from the group consisting of D&C Red 27, D&C Red 28, Opatint-OD 1646, Opatint-OD 1774, CAS#13473-26-2, 18472-87-2, 16423-68-0, 548-26-5, 2379-74-0, 915-67-3, 25956-17-6, fluorescein dyes with chlorine and/or bromine, tetrabromo-tetrachloro-fluorescein, disodium salt of tetrabromo-tetrachloro-f fluorescein, and mixtures thereof.

15. The method of claim 14 wherein the colorant level is from about 0.02% to about 2% by weight of the composition.

16. The method of claim 15 wherein the colorant is selected from the group consisting of Opatint OD 1646, fluorescein dyes with chlorine and/or bromine, tetrabromo-tetrachloro-fluorescein, disodium salt of tetrabromo-tetrachloro-fluorescein, and mixtures thereof.

* * * * *

UNITED STATES PATENT AND TRADEMARK OFFICE
CERTIFICATE OF CORRECTION

PATENT NO. : 6,475,498 B1
DATED : November 5, 2002
INVENTOR(S) : Jayanth Rajaiah et al.

It is certified that error appears in the above-identified patent and that said Letters Patent is hereby corrected as shown below:

<u>Title page,</u>
Item [56], U.S. PATENT DOCUMENTS, "5,334,375 A" "Nabl" should read -- Nabi --

Signed and Sealed this

Fifth Day of August, 2003

JAMES E. ROGAN
*Director of the United States Patent and Trademark Office*